(12) United States Patent
Hartmann

(10) Patent No.: US 6,482,185 B1
(45) Date of Patent: Nov. 19, 2002

(54) INJECTION DEVICE COMPRISING A PEN

(75) Inventor: Michael Hartmann, Melsungen (DE)

(73) Assignee: B. Braun Melsungen AG, Melsungen (DE)

(*) Notice: Subject to any disclaimer, the term of this patent is extended or adjusted under 35 U.S.C. 154(b) by 0 days.

(21) Appl. No.: 09/528,443

(22) Filed: Mar. 17, 2000

(30) Foreign Application Priority Data

Mar. 17, 1999 (DE) .................................. 299 04 864 U

(51) Int. Cl.[7] .................................................. A61M 5/00
(52) U.S. Cl. ........................ 604/189; 604/208; 604/211
(58) Field of Search ............................... 604/189, 207, 604/208, 211

(56) References Cited

U.S. PATENT DOCUMENTS

| | | | |
|---|---|---|---|
| 5,569,212 A | * | 10/1996 | Brown ........................ 604/207 |
| 5,704,922 A | * | 1/1998 | Brown ........................ 604/207 |
| 5,720,733 A | * | 2/1998 | Brown ........................ 604/207 |
| 5,782,814 A | * | 7/1998 | Brown et al. ............... 604/207 |
| 5,792,117 A | * | 8/1998 | Brown ........................ 604/207 |
| 6,068,615 A | * | 5/2000 | Brown et al. ............... 604/207 |

* cited by examiner

*Primary Examiner*—Gerald A. Michalsky
(74) *Attorney, Agent, or Firm*—Diller, Ramik & Wight PC

(57) ABSTRACT

An injection device comprises a pen (10) with a syringe (13) to be emptied. The dose expelled from the syringe is set by means of a dose setting device (17). For people with an impaired vision, the setting of the dose is rather difficult. Therefore, an external display apparatus (30) is provided that may be set to the pen (10). Via contacts (21) and counter contacts (34), information about the dose is transmitted to the display apparatus (30) and shown on a large display (32).

13 Claims, 4 Drawing Sheets

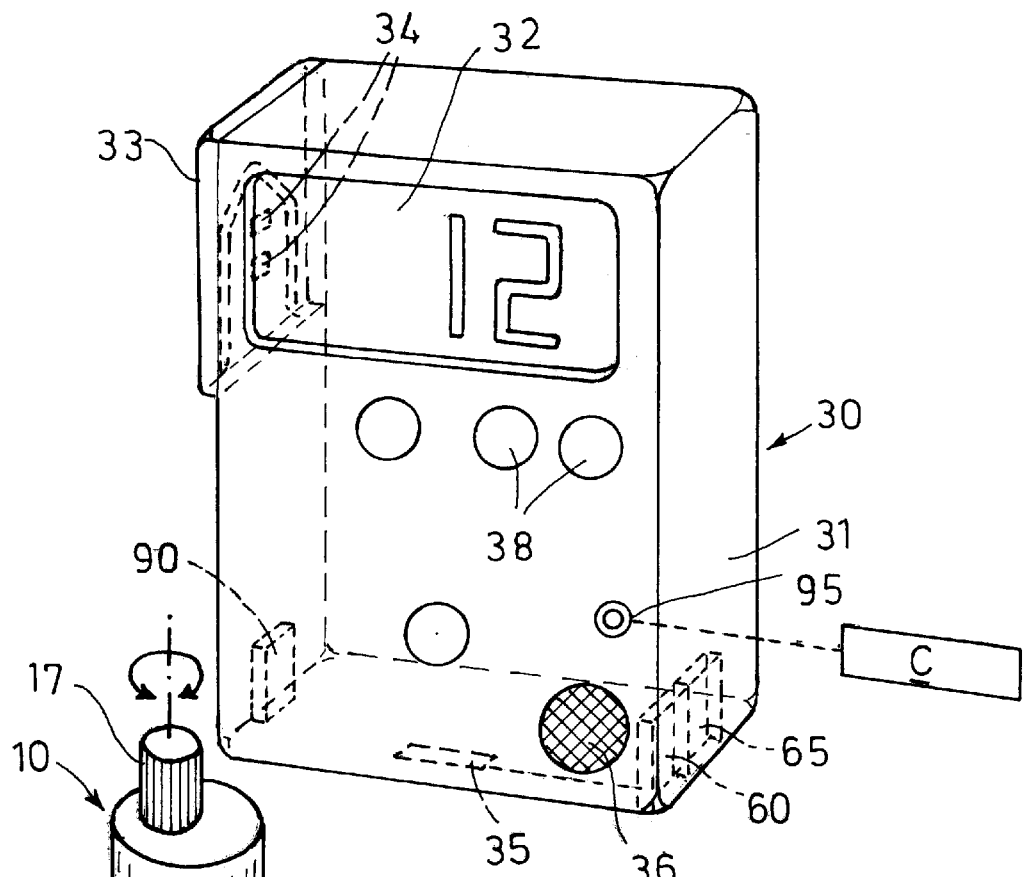
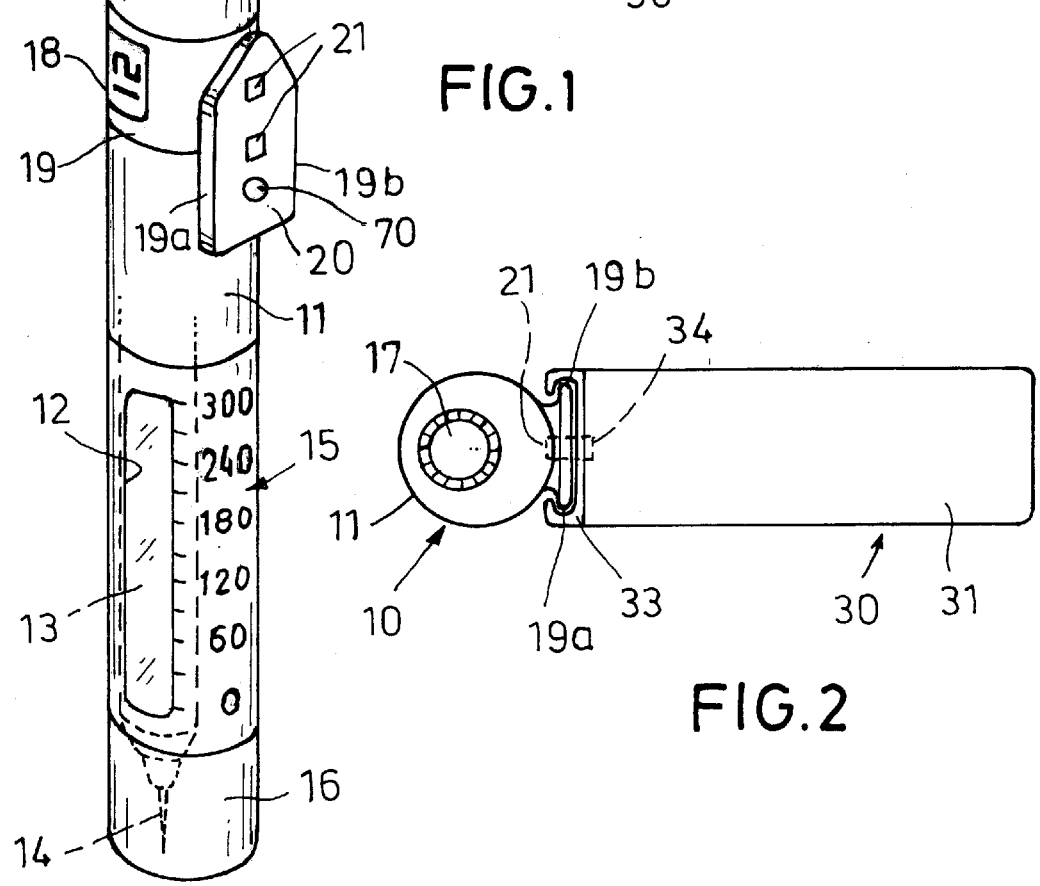
FIG.1
FIG.2

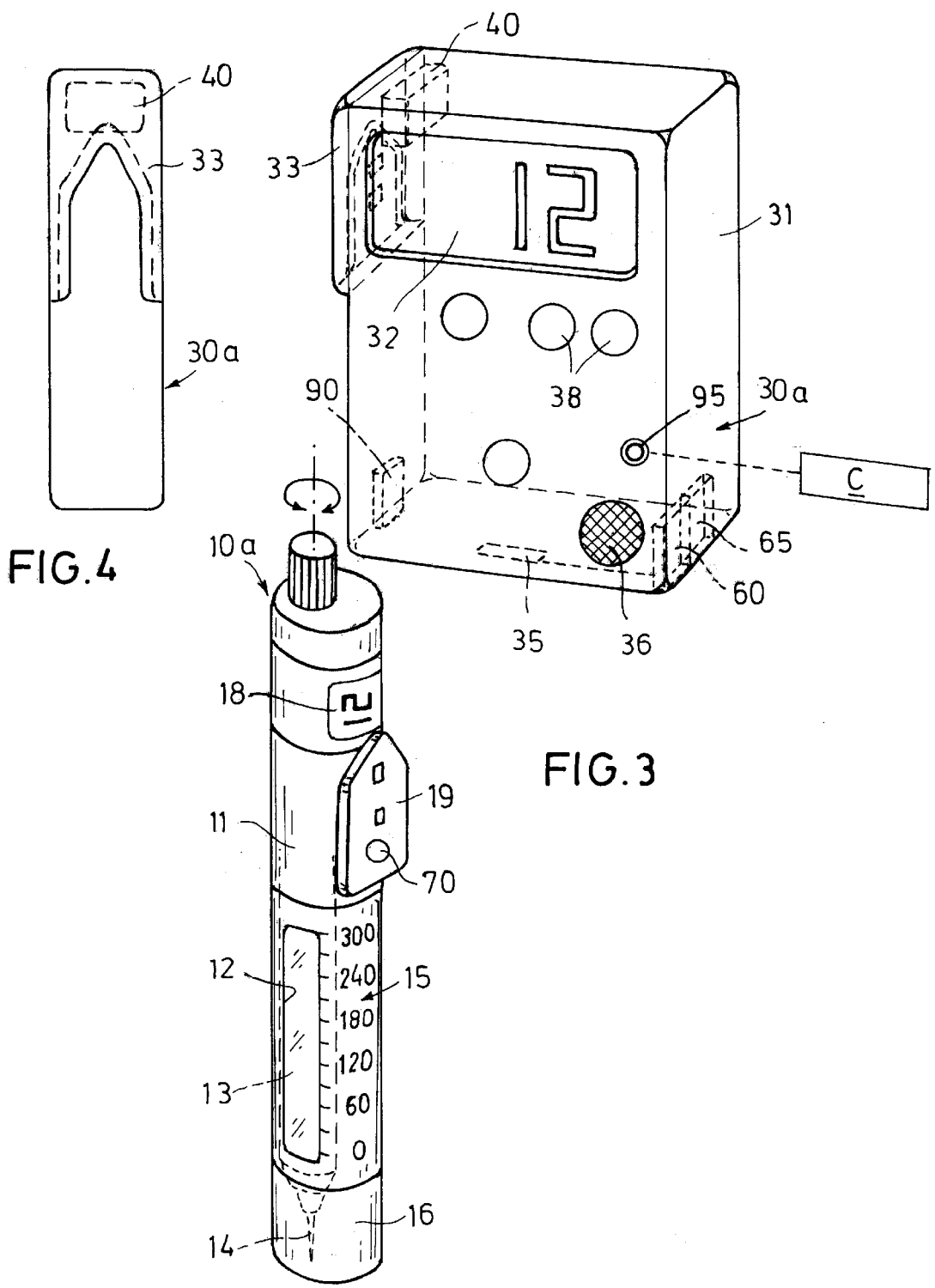

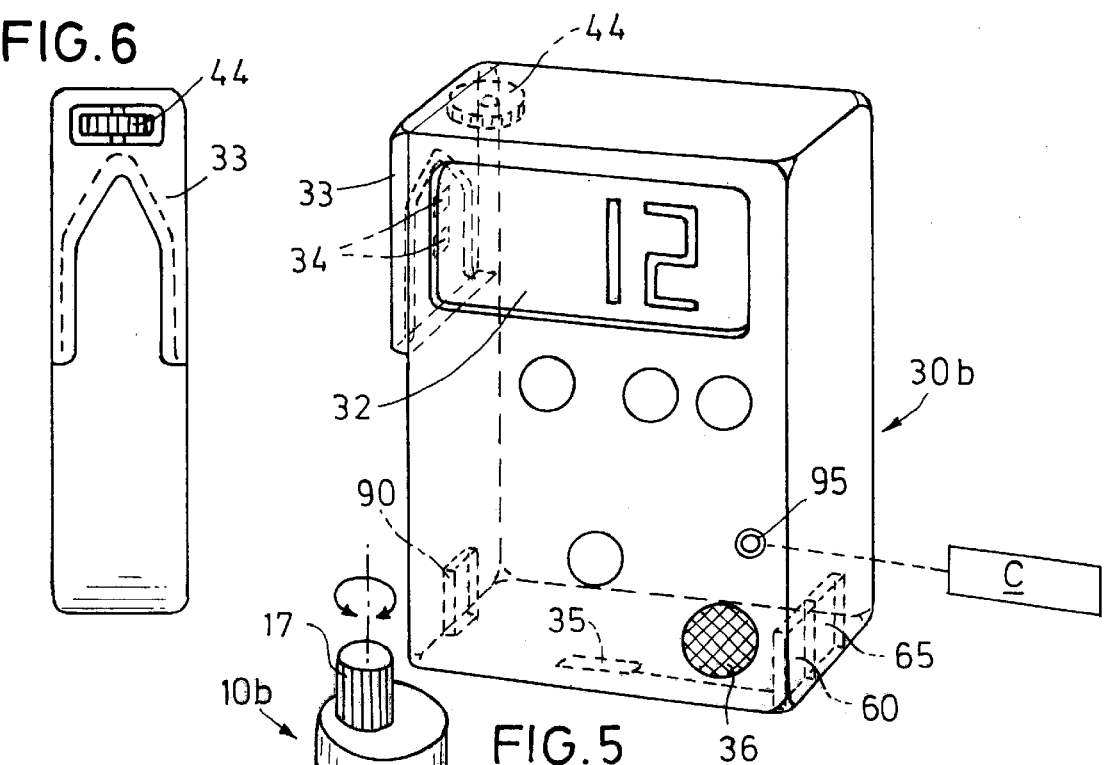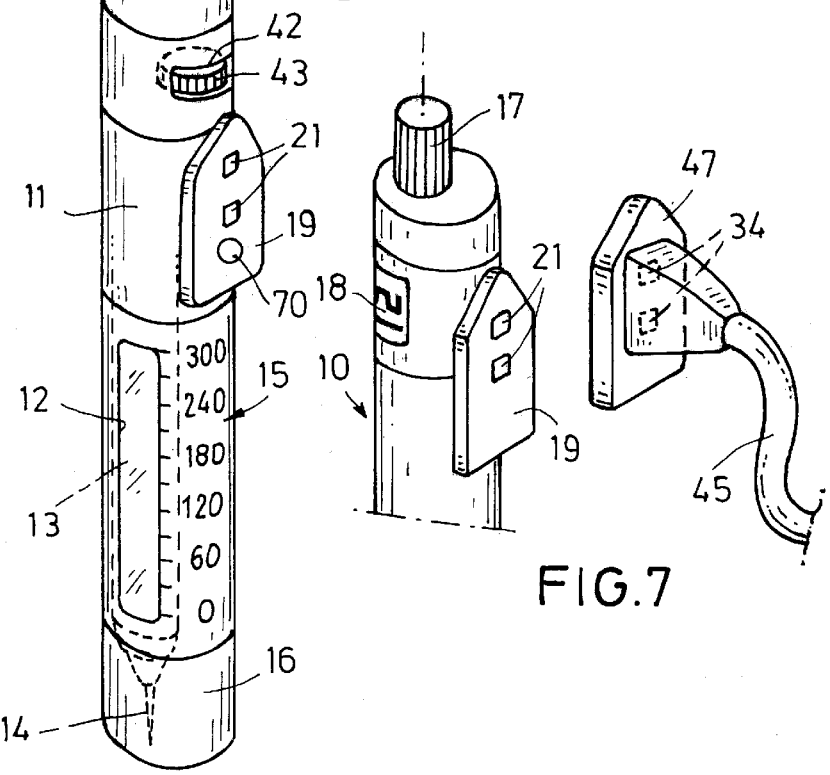

INJECTION DEVICE COMPRISING A PEN

BACKGROUND OF THE INVENTION

The present invention refers to an injection device with a pin-shaped housing having a manually operated device for setting a dose.

Injection devices with a pin-shaped housing are known with which patients can inject insulin themselves, the injection dose being set by means of a manually operated dose setting device. Corresponding to the dose set, a preset amount of the contents of the syringe are expelled from from the syringe when an actuating button is operated. The dose setting device comprises a rotatable hand knob provided at the end of the pin-shaped housing. Further, the housing has a display indicating the dose set on a scale or a LCD.

There is a problem that people with impaired vision have great difficulty setting or controlling the dose. Thus, wrong dosing may occur.

SUMMARY OF THE INVENTION

It is an object of the present invention to provide an injection device with a pin-shaped housing (pen), which allows a dose set to be easily read also by people with impaired vision.

In the present injection device, the pin-shaped housing is coupled to an external display device that receives information on the respective dose set and displays the dose on a rather large display. Thus, the size of the display device is not limited to the narrow pen shape of the pin-shaped housing. On the other hand, the advantages of the pin-shaped housing, i.e. its being easy to take along and its simple handling, can be maintained. The pin-shaped housing is coupled with the display device only to set the dose.

Existing technology may be used for the display device. For insulin injecting diabetics, the display of an existing blood sugar measuring apparatus can be used to display the setting of a dose. It is further possible to connect economic one-way pens with a comfortable and large reusable display apparatus that can also be suited for storing data, among other features. Using the external display, one can do without batteries in a one-way pen. The display apparatus may comprise a language module for acoustically outputting the dose set. The dose set is stored together with the time, the date and the kind of medication (e.g. insulin preparation).

Each display apparatus may provide storage possibilities for several people. A person is identified by a defined feature. In the display apparatus, the individual pin-shaped housings (pens) are each associated with individual contents (insulin preparations). The display apparatus may contain further person-related data. For diabetics, one may input e.g. the bread units, the calculated insulin amount for covering one bread unit, individual therapeutic goals of blood sugar control, particularities of metabolism and profiles of action of the different insulin preparations, or these values may be received from a PC. Due to its storage capabilities, the external display can be used by a physician or medical personnel to yield exact information on the kind and time of an injection. From the data associated with a certain person, a proposed insulin dose may be calculated using a measured blood sugar rate. This dose is then set at the pen, using the same display apparatus.

It is the principle idea of the present invention to facilitate the setting of a dose in a pen by using a separate display. The data transfer between the pen and the display apparatus allows for other functions besides the optical indication of the dose setting, such as an acoustic indication of the dose setting, the storing of the injection amount with time and date, an illuminated display, the storing of the injected preparation and, overall, an automatic data management.

The data transfer from the pen to the display apparatus may be effected in different ways, such as electrically, optically or mechanically. Here, it is possible to connect the pen directly to the housing of the display apparatus or to provide the display apparatus with a plug connected with the pen. In each case, a fool-proof means should be provided that allows the pen and the display apparatus to be coupled only in the correct position (polarity).

It is also possible to provide the pen with a code to be recognized by the display apparatus so that the display apparatus will always know with which pen or pen type it cooperates.

It is possible to provide the display apparatus and/or the pen with a voltage supply, where the voltage supply of one device may also supply the other.

According to another aspect of the invention, the display apparatus sets a dose at the pen. This may be accomplished by providing the display apparatus with a force transmission device to which the pen is connected. If the display apparatus is a blood sugar measuring apparatus, for example, it can calculate the dose from the measured blood sugar rate and further stored parameters, and it can automatically take care that this dose is set at the pen. Thereafter, the pen is removed from the display apparatus.

BRIEF DESCRIPTION OF THE DRAWINGS

The following is a detailed description of embodiments of the invention with reference to the accompanying drawings.

In the figures

FIG. 1 is a schematic perspective view of the injection device with pen and display apparatus electrically coupled, FIG. 2 is a front view of the pen and the display apparatus when coupled, FIG. 3 illustrates a second embodiment of the injection device with optic coupling, FIG. 4 is a front view of FIG. 3, FIG. 5 illustrates a third embodiment of the injection device with mechanic coupling, FIG. 6 is a side elevational view of the coupling side of the display apparatus in FIG. 5, FIG. 7 shows a detail of the display apparatus being coupled using an adapter cable.

DETAILED DESCRIPTION OF PREFERRED EMBODIMENTS OF THE INVENTION

Figure 8:
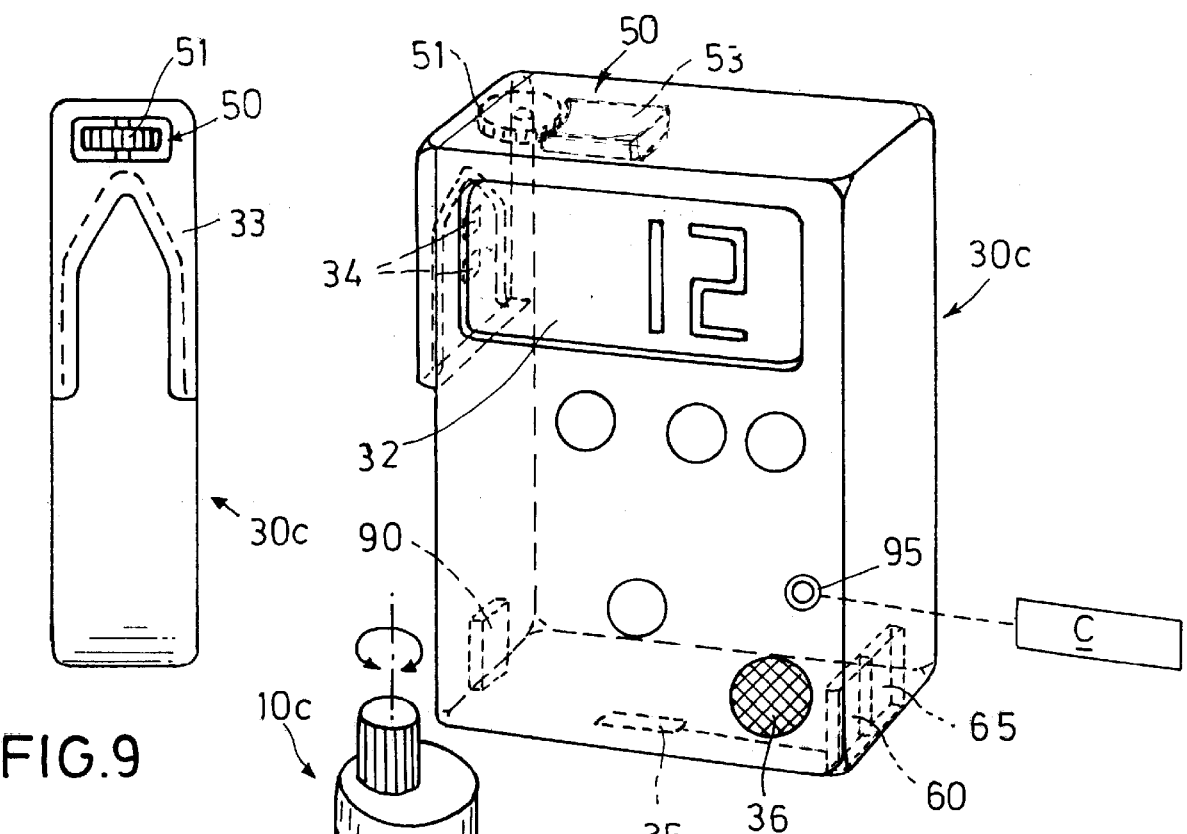
FIG. 8 illustrates a fourth embodiment of the injection device wherein the display apparatus effects the dose setting at the pen.

FIGS. 1 and 2 illustrate a pen 10 having a thin elongate pin-shaped housing 11. The wall of the housing 11 is provided with a window 12 through which a part of a pre-filled cartridge 13 inserted into the housing 11 is visible. This cartridge includes a cylinder and a piston movable therein. A medication such as insulin is expelled from the cartridge 13. To this avail, the front end of the cartridge 13 has a hypodermic needle 14. A scale 15 is provided at the window 12 indicating the residual amount left in the cartridge.

At the front end, the housing 11 has a removable protective cap 16. With the protective cap 16 removed, the hypodermic needle 14 is exposed. The user may then puncture the body with the hypodermic needle 14 and may then expel a predetermined amount of liquid from the syringe 13.

The dose is set at a dose setting device 17. By turning this knob, the amount of liquid expelled from the syringe 13 in one expelling operation can be set. Turning the knob changes the extent of advance of a piston in an expelling operation. The movement of the piston is obtained by spring forces. The liquid is expelled from the syringe by pressing an operating knob at the side of the housing 11.

The volume of set at the dose setting device for one expelling operation is shown on a display 18 provided at the housing 11. This display may be an LCD indicating the volume in milliliters. The housing 11 includes a battery for powering the display 18.

In the rear portion, the housing 11 has a longitudinally extending linear guide 19. A flattened portion 20 is provided between the guide rails 19a, 19b of this linear guide, and contacts 21 are provided within the perimeter of the flattened portion 20.

The display apparatus 30 is provided in combination with the pen 10. This device is a separate apparatus with a housing 31 having a large display 32. In a minor side surface of the housing 31, a shallow receptacle 33 is formed that may be brought into fitting engagement with a linear guide 19 of the pen 10. Small counter contacts 34 are arranged in the receptacle 33 that match the contacts 21 of the pen. Thus, the housing 31 may be pushed laterally onto the pen 10, the contacts 21 engaging the counter contacts 34. The linear guide 19 extends in parallel to the longitudinal axis of the pen 10 so that the display apparatus 30 is pushed onto the pen in the longitudinal direction thereof, both parts then forming a rigid unit.

The dose setting device 17 comprises an encoder (not illustrated) supplying the contacts 21 with an electric signal representing the dose set. This signal is transmitted to the display apparatus 30 via the counter electrodes 34 and—possibly after a corresponding conversion—displayed on the large display 32. Thus, the user can readily read the injection dose set on the large display 32 without having to rely on the small display 18 of the pen 10. The display may be in milliliters or in (insulin) units.

Another possibility for an electric signal transmission lies in generating a pulse (or a pulse gap) in the pen for each dose unit when setting the doses. The number of pulses thus generated is shown on the display 32. The display apparatus 30 has a power supply of its own applied to the contacts 21 of the pen, the operation of the dose setting device 17 causing corresponding pulses. The display apparatus 30 detects the correct zero position in the pen 10 at the beginning of the dose setting by means of a third contact (not illustrated) that is conductive only in this position, or it detects this position by a defined voltage drop (contact resistance) characteristic of the zero position. The dose setting is corrected by turning the setting device 17. In order to detect the direction of turning, the signal for each unit is composed of two different pulses (short/long or weak/strong). The sequence in time of the two different pulses shows the direction of turning.

In the present case, the display apparatus 30 at the same time serves as a blood sugar testing device that is substantially structured as a device available from B. Braun Petzold GmbH under the designation Omnitest Sensor. This blood sugar testing device has an insertion slot 35 for inserting a test strip provided with a blood sample. The display 32 will then show the blood sugar rate. In combination with the pen 10, the blood sugar measuring device is also used as a display device for the dose indication of the pen. Thus, an additional display device may be omitted.

The housing 31 of the display apparatus 30 is further provided with a speaker 36. The device includes a voice processor that converts the dose indication into spoken acoustic information so that the dose indication also becomes audible.

A slide may be provided at the housing 31, which may be slid over the receptacle 33 and covers the same in the closed state so that the counter contacts 34 are protected. The cover opens automatically when the pen is inserted and closes automatically when the pen is withdrawn. Moreover, the housing 31 has various operating knobs 38.

The mechanic coupling of the pen 10 to an external display apparatus 30 requires the pen to of asymmetric shape to guarantee a perfect positioning of the display apparatus 30. The display apparatus is structured such that after the locking of the pen 10, the dose setting device 17 remains easily accessible. Coupling the pen in is possible with and without the protective cap 16. The display 18 of the pen should also remain visible when the display apparatus 30 is connected.

For a detection of the respective pen type, the pen may be provided with corresponding codes, for example in the form of projections or indentations. They may also be breakable flaps or conductive contacts at the pen surface detected by electric contacts of the display apparatus.

The embodiment represented in FIGS. 3 and 4 uses a slightly modified pen 10a. In the pen 10a, the display 18 is arranged adjoining the linear guide 19 so that the latter is covered by the display apparatus 30a. The transmission of the dose set from the pen 10a to the display apparatus 30a is done optically. The display apparatus 30a is provided with an optical sensor 40 directly opposite the display 18. Consequently, the same indication is generated in the display 32.

Another possibility is to also provide the sensor 40 with a light emitter irradiating light on the display 18. During the dose setting at the pen 10a, the reflection properties of in the window of the display 18 change for every unit. The changing reflection is detected by the sensor 40.

In the embodiment of FIGS. 5 and 6, the transmission of the dose value is effected mechanically. Here, the pen is provided with a slot 42 exposing a part of the circumference of a pinion 43. Another pinion 44 is supported in the display apparatus 30b such that a part of its circumference protrudes into the receptacle 33. When coupling the display apparatus 30b to the pen 10b, the pinions 43 and 44 come to mesh. The rotary movement of the setting device 17 is thus transmitted to the display apparatus 30b by mechanically cooperating coupling means in the form of pinions 43, 44.

In the embodiment of FIG. 7, the pen 10 is designed in the same way as in FIG. 1, however, the housing of the display apparatus 30 is not coupled directly to the housing of the pen. Rather, the display apparatus 30 comprises a cable 45 with a plug 47 including the counter contacts 34 that are to be connected with the contacts 21 of the pen. Thus, it is not necessary to lift the housing of the display apparatus and to couple it to the pen. A similar coupling of a separate housing to a pen is also possible with the optic scanning according to FIG. 3. Here, the sensor 40 may be accommodated in a plug connected to the housing of the display apparatus through a light conducting cable or electrically.

Figure 9:
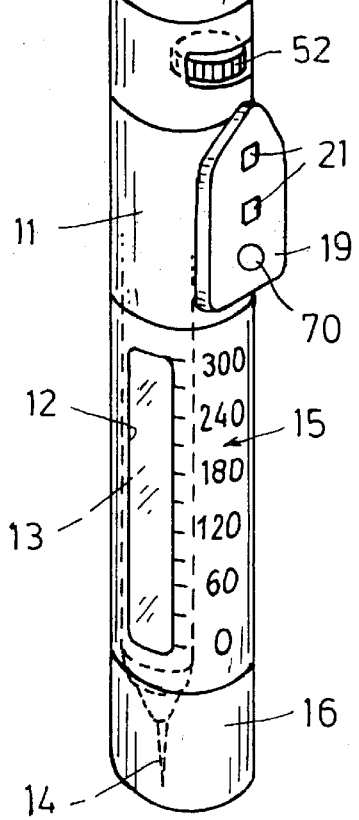
FIG. 9 is a side elevational view of the coupling side of the display apparatus of FIG. 8.

FIGS. 8 and 9 illustrate an embodiment wherein the display apparatus 30c includes a dose setting device 50. The display apparatus 30c again is a blood sugar measuring device with a slot 35 for inserting a measuring strip. From the test result derived from the measuring strip and from the patient related data input by hand, the display apparatus 30c calculates the amount of insulin to be set. When the display apparatus 30c is coupled to the pen 10c, a pinion 51 of the dose setting device 50 comes to mesh with a pinion 52 of the pen 10c. By turning the pinion 52, the dose calculated by the display apparatus 30c is set in the pen 10c. The pinion 51 of the display apparatus 30c is driven by a motor 53, preferably a stepper motor.

The injection device may also include one or more of the following:
- means (60) for calculating the single injection predetermined volume dose from a measured blood sugar rate,
- a pen which lacks a power source and is supplied power from a power source (65) of the external display apparatus,
- an external display apparatus which lacks a power source but is supplied power from a power source (70) of the pen,
- means (90) for identifying a specific pen, patient and dose, and
- means (95) for connecting to the external display apparatus and an external computer (C) for data transfer.

What is claimed is:

1. An injection device comprising in combination a pen (10, 10a, 10b, 10c) having a pin-shaped housing (11) accommodating a syringe (13) and an external display apparatus (30, 30a, 30b, 30c); means (17, 50) for setting a predetermined volume of liquid which is to be expelled from said syringe (13) by a single injection dose, means (21, 34; 43, 44) responsive to said setting means (17, 50) for transmitting the set single injection predetermined volume dose from one of the pen (10, 10b and 10c) and the external display apparatus (30, 30a, 30b, 30c) to the respective external display apparatus (30, 30a, 30b, 30c) and the pen (10, 10b and 10c), and said external display apparatus (30, 30a, 30b, 30c) including means (32) for displaying the set single injection predetermined volume dose as a larger readily read display (32).

2. The injection device as defined in claim 1 including means (35) for measuring blood sugar, and said setting means (50) is responsive to said blood sugar measuring means (35).

3. The injection device as defined in claim 1 including means (35) for measuring blood sugar, said setting means (50) is responsive to said blood sugar measuring means (35), and said transmitting means (50) transmits the single injection predetermined volume dose from said external display apparatus (30, 30a, 30b, 30c) to said pen (10, 10b, 10c).

4. The injection device as defined in claim 1 wherein said setting means (50) is defined by mechanical force transmitting elements (51, 52) of the respective external display apparatus (30c) and the pen (10c).

5. The injection device as defined in claim 1 wherein said setting means (50) comprises mechanical force transmitting elements (51, 52) of the respective external display apparatus (30c) and the pen (10c), and means (53) driving the mechanical force transmitting element (51) of said external display apparatus (30c).

6. The injection device as defined in claim 1 wherein said setting means (50) is defined at least in part (51) by said external display apparatus (30c).

7. The injection device as defined in claim 1 wherein said external display apparatus (30c) includes means (60) for calculating the single injection predetermined volume dose from a measured blood sugar rate.

8. The injection device as defined in claim 1 wherein said external display apparatus (30c) includes means (60) for calculating the single injection predetermined volume dose from a measured blood sugar rate, and said transmitting means (50) transmits the single injection predetermined volume dose on the basis of said calculating means (60).

9. The injection device as defined in claim 1 wherein the pen (10, 10a, 10b, 10c) lacks a power source and is supplied power from a power source (65) of said external display apparatus (30, 30a, 30b, 30c).

10. The injection device as defined in claim 1 wherein the external display apparatus (30, 30a, 30b, 30c) lacks a power source and is supplied power from a power source (70) of said pen.

11. The injection device as defined in claim 1 wherein said external display apparatus (30c) includes means (36) for providing an acoustic indication of the single injection predetermined volume dose.

12. The injection device as defined in claim 1 wherein said external display apparatus (30, 30a, 30b, 30c) includes means (90) for identifying a specific pen, a specific patient and a specific dose.

13. The injection device as defined in claim 1 wherein said external display apparatus (30, 30a, 30b, 30c) includes means (95) for connecting thereto an external computer (C) for data transfer.

* * * * *